(12) United States Patent
Watkins et al.

(10) Patent No.: US 7,340,087 B2
(45) Date of Patent: Mar. 4, 2008

(54) EDGE INSPECTION

(75) Inventors: Cory Watkins, Chanhassen, MN (US);
Mark Harless, Plymouth, MN (US);
Francy Abraham, Singapore (SG)

(73) Assignee: Rudolph Technologies, Inc., Flanders, NJ (US)

( * ) Notice: Subject to any disclaimer, the term of this patent is extended or adjusted under 35 U.S.C. 154(b) by 630 days.

(21) Appl. No.: 10/890,762

(22) Filed: Jul. 14, 2004

(65) Prior Publication Data
US 2005/0036671 A1    Feb. 17, 2005

Related U.S. Application Data

(60) Provisional application No. 60/486,953, filed on Jul. 14, 2003.

(51) Int. Cl.
*G06K 9/00* (2006.01)
*G01N 21/86* (2006.01)

(52) U.S. Cl. .................. 382/145; 250/559.36

(58) Field of Classification Search ............. 382/145, 382/147, 149, 266, 274–275, 312; 356/237.1; 250/559.36, 559.46; 341/13; 257/797
See application file for complete search history.

(56) References Cited

U.S. PATENT DOCUMENTS

| | | | |
|---|---|---|---|
| 4,328,553 A | 5/1982 | Fredriksen et al. | |
| 4,464,705 A | 8/1984 | Horowitz | |
| 4,644,172 A | 2/1987 | Sandland et al. | |
| 4,764,969 A * | 8/1988 | Ohtombe et al. | 382/148 |
| 4,823,394 A | 4/1989 | Berkin et al. | |
| 5,091,963 A | 2/1992 | Litt et al. | |
| 5,497,381 A | 3/1996 | O'Donoghue et al. | |
| 5,547,537 A | 8/1996 | Reynolds et al. | |
| 5,592,295 A | 1/1997 | Stanton et al. | |
| 5,640,200 A | 6/1997 | Michael | |
| 5,641,960 A | 6/1997 | Okubo et al. | |
| 5,787,190 A | 7/1998 | Peng et al. | |
| 5,822,055 A | 10/1998 | Tsai et al. | |
| 5,850,466 A | 12/1998 | Schott | |
| 5,852,413 A * | 12/1998 | Bacchi et al. | 341/13 |
| 5,856,844 A | 1/1999 | Battermann et al. | |
| 5,859,698 A | 1/1999 | Chau et al. | |
| 5,917,588 A | 6/1999 | Addiego | |
| 5,949,901 A | 9/1999 | Nichani et al. | |
| 6,137,303 A | 10/2000 | Deckert et al. | |
| 6,140,254 A | 10/2000 | Endisch et al. | |
| 6,147,357 A | 11/2000 | Nicolescu | |
| 6,153,361 A | 11/2000 | Liu et al. | |
| 6,314,379 B1 | 11/2001 | Hu et al. | |
| 6,324,298 B1 | 11/2001 | O'Dell et al. | |

(Continued)

OTHER PUBLICATIONS

International Search Report mailed Mar. 2, 2005 (3 pgs).

*Primary Examiner*—Kanjibhai Patel
(74) *Attorney, Agent, or Firm*—Dicke, Billig & Czaja, PLLC

(57) ABSTRACT

A semiconductor inspection tool comprises an edge top camera for obtaining images of a top edge of a wafer, an edge normal camera for obtaining images of a normal edge of the wafer, and a controller for receiving the images of the top edge of the wafer and the images of the normal edge of the wafer and for analyzing the images of the top edge of the wafer and the images of the normal edge of the wafer for wafer edge defects.

36 Claims, 9 Drawing Sheets

U.S. PATENT DOCUMENTS

| | | |
|---|---|---|
| 6,412,326 B1 | 7/2002 | Hubbard et al. |
| 6,420,792 B1 * | 7/2002 | Guldi et al. ................. 257/797 |
| 6,432,800 B2 | 8/2002 | Park |
| 6,565,920 B1 | 5/2003 | Endisch |
| 6,640,151 B1 | 10/2003 | Somekh et al. |
| 6,702,302 B2 * | 3/2004 | Smedt et al. ................. 279/106 |
| 6,708,074 B1 | 3/2004 | Chi et al. |
| 6,778,258 B2 * | 8/2004 | del Puerto et al. ............ 355/72 |
| 6,906,794 B2 * | 6/2005 | Tsuji ....................... 356/237.4 |
| 7,149,341 B2 * | 12/2006 | Hayashi et al. ............. 382/145 |
| 2003/0030050 A1 | 2/2003 | Choi |
| 2003/0202178 A1 | 10/2003 | Tsuji et al. |

\* cited by examiner

EDGE INSPECTION

CROSS-REFERENCE TO RELATED APPLICATIONS

This application claims the benefit of U.S. Provisional Application Ser. No. 60/486,953, filed Jul. 14, 2003.

BACKGROUND

1. Technical Field

The present invention relates to an inspection system that inspects the edge of a semiconductor wafer or like substrate such as a microelectronics substrate.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors. To assist these demands, better inspection is necessary to increase yields. One area that has been generally ignored is the edge of the semiconductor wafer, and it is believed that inspection of such edge area will lead to better information on defects, thereby enabling improved process control and improved wafer yields.

In the past, when attempts to inspect the wafer edge were made, the inspection was generally performed manually with the naked eye of a human operator. As with all human inspection, repeatability, training, and capture rate are subject to flux. It has recently been discovered that wafer edge inspection is important for detecting delamination of thin films, chipping and cracking of the wafer, resist removal metrology, and particle detection, all of which cause yield issues in a modern fab. Furthermore, the edge of the wafer is a leading indicator of process status, and by monitoring the edge of the wafer for changes in appearance, tighter process control can be implemented.

One proposed solution includes laser/analog detector technology that looks directly at the edge normal of the wafer. This solution provides limited benefits in detecting particles and chip-outs, but is limited in classifying defects since the solution does not perform image processing. The market is looking for continued improvement in edge inspection.

SUMMARY

One embodiment of the present invention provides a semiconductor inspection tool. The semiconductor inspection tool comprises an edge top camera for obtaining images of a top edge of a wafer, an edge normal camera for obtaining images of a normal edge of the wafer, and a controller for receiving the images of the top edge of the wafer and the images of the normal edge of the wafer and for analyzing the images of the top edge of the wafer and the images of the normal edge of the wafer for wafer edge defects.

BRIEF DESCRIPTION OF THE DRAWINGS

Preferred embodiments of the invention, illustrative of the best mode in which applicant has contemplated applying the principles, are set forth in the following description and are shown in the drawings and are particularly and distinctly pointed out and set forth in the appended claims.

Similar numerals refer to similar parts through the drawings.

DETAILED DESCRIPTION

Figure 1:
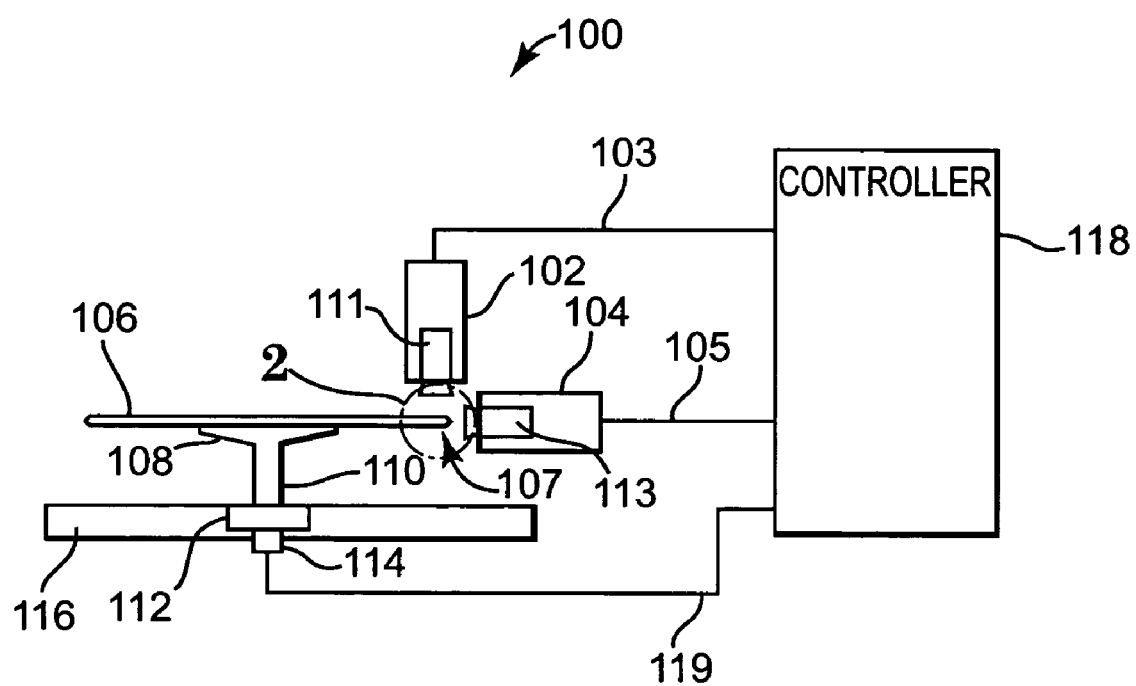
FIG. 1 is a schematic diagram illustrating one embodiment of an edge inspection system.

FIG. 1 is a schematic diagram illustrating one embodiment of an edge inspection system 100. Edge inspection system 100 includes an edge top sensor 102, an edge normal sensor 104, a controller 118, a base 116, and a stage 110. Top edge sensor 102 includes a camera 111, and normal edge sensor 104 includes a camera 113. Stage 110 includes a motor 112, an encoder 114, and a support plate 108. Motor 112 is coupled to encoder 114 and support plate 108 to rotate support plate 108. Encoder 114 provides counts for controlling the position of motor 112. Support plate 108 supports a wafer 106 for inspecting an edge 107 of wafer 106. Controller 118 is electrically coupled to top edge sensor 102 through communication link 103, normal edge sensor 104 through communication link 105, and staging 110 through communication link 119. Controller 118 controls edge top sensor 102, edge normal sensor 104, and staging 110 for inspecting edge 107 of wafer 106.

Figure 2:
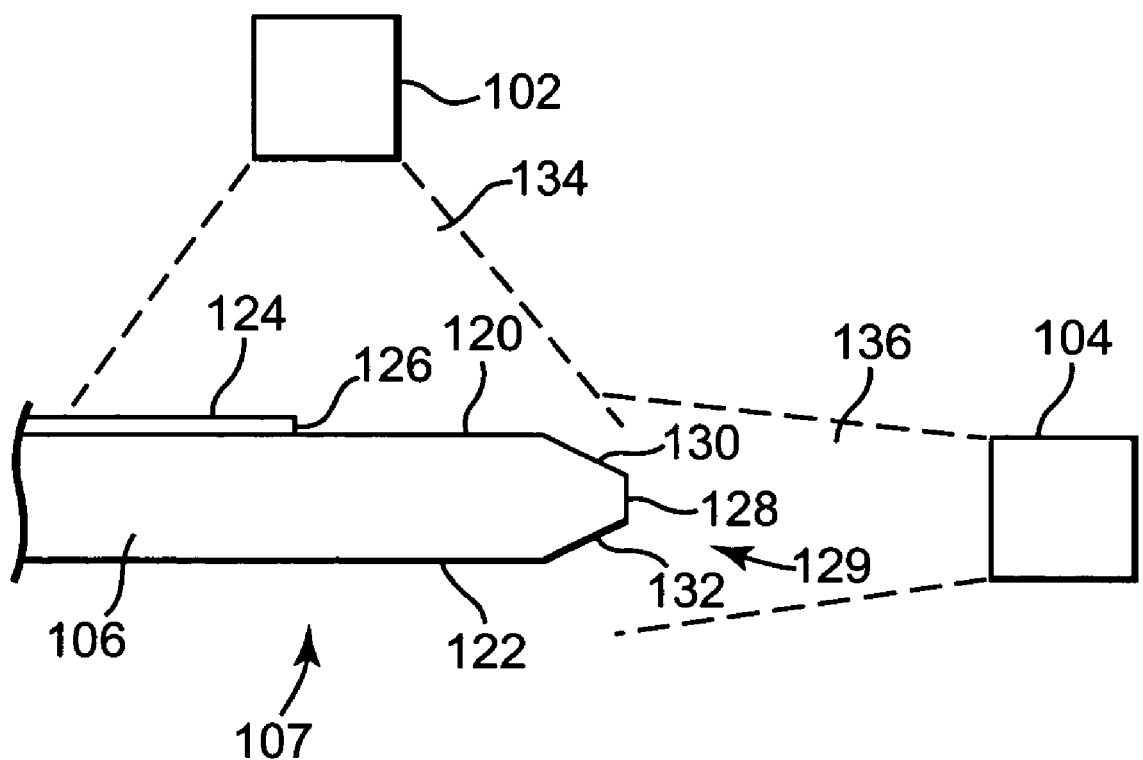
FIG. 2 is a schematic diagram illustrating the indicated portion of the edge inspection system illustrated in FIG. 1 in more detail.

FIG. 2 is a schematic diagram illustrating the indicated portion of edge inspection system 100 illustrated in FIG. 1 in more detail. FIG. 2 illustrates edge top sensor 102, normal edge sensor 104, and edge 107 of wafer 106. Edge 107 of wafer 106 includes resist layer 124 having an edge bead removal (EBR) line 126, edge exclusion region 120, wafer edge bevel 129, and wafer bottom 122. Wafer edge bevel 129 includes top bevel 130, wafer edge normal 128, and bottom bevel 132. Edge top sensor 102 has a field of view as indicated at 134. Edge normal sensor 104 has a field of view as indicated at 136. Edge inspection system 100 inspects and/or measures along edge 107 of wafer 106 including resist layer 124, edge exclusion region 120, top bevel 130, wafer edge normal 128, and bottom bevel 132.

Figure 3:
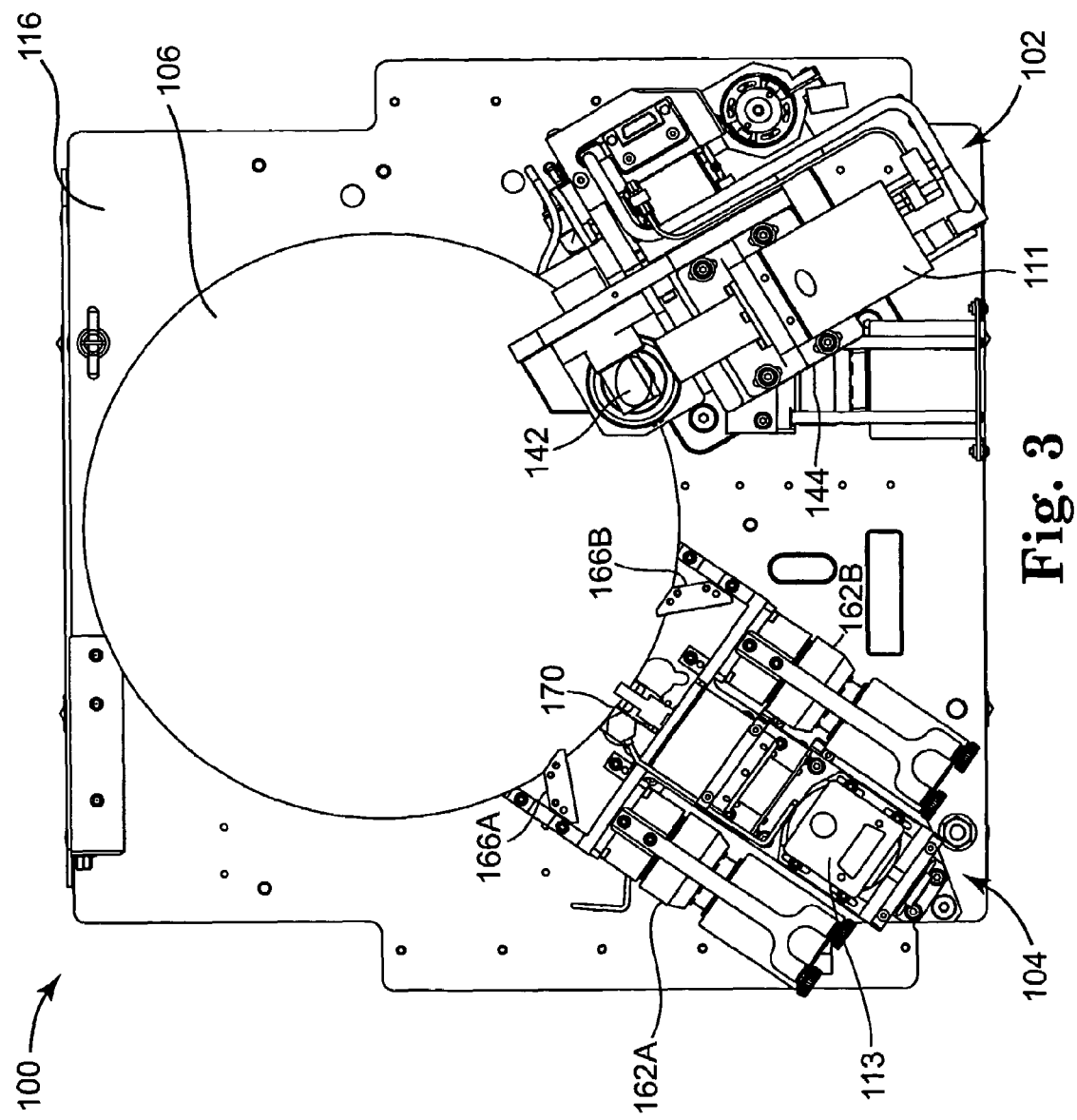
FIG. 3 is a top view illustrating one embodiment of the edge inspection system.
Figure 4:
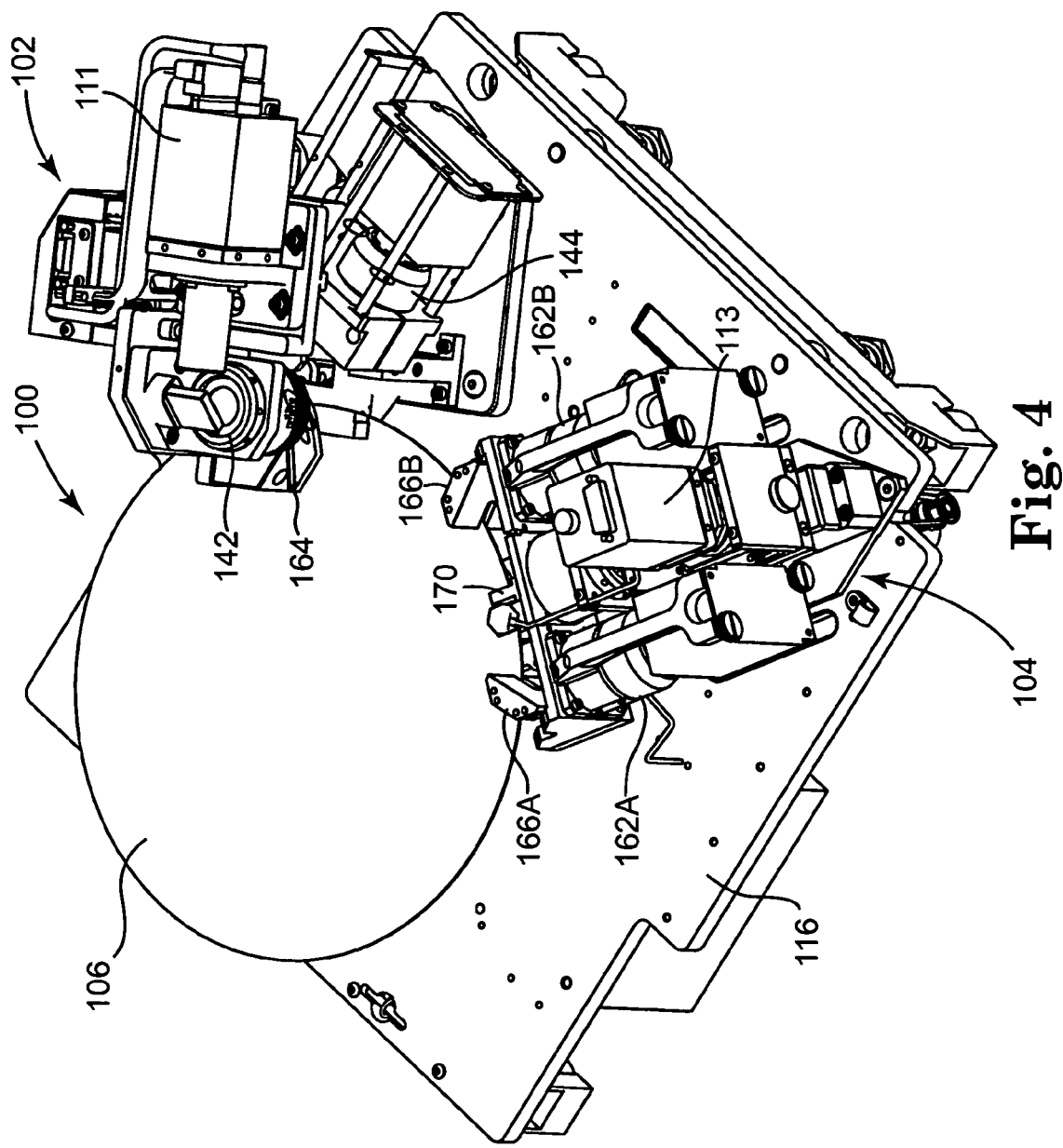
FIG. 4 is an angled perspective view illustrating one embodiment of the edge inspection system.
Figure 5:
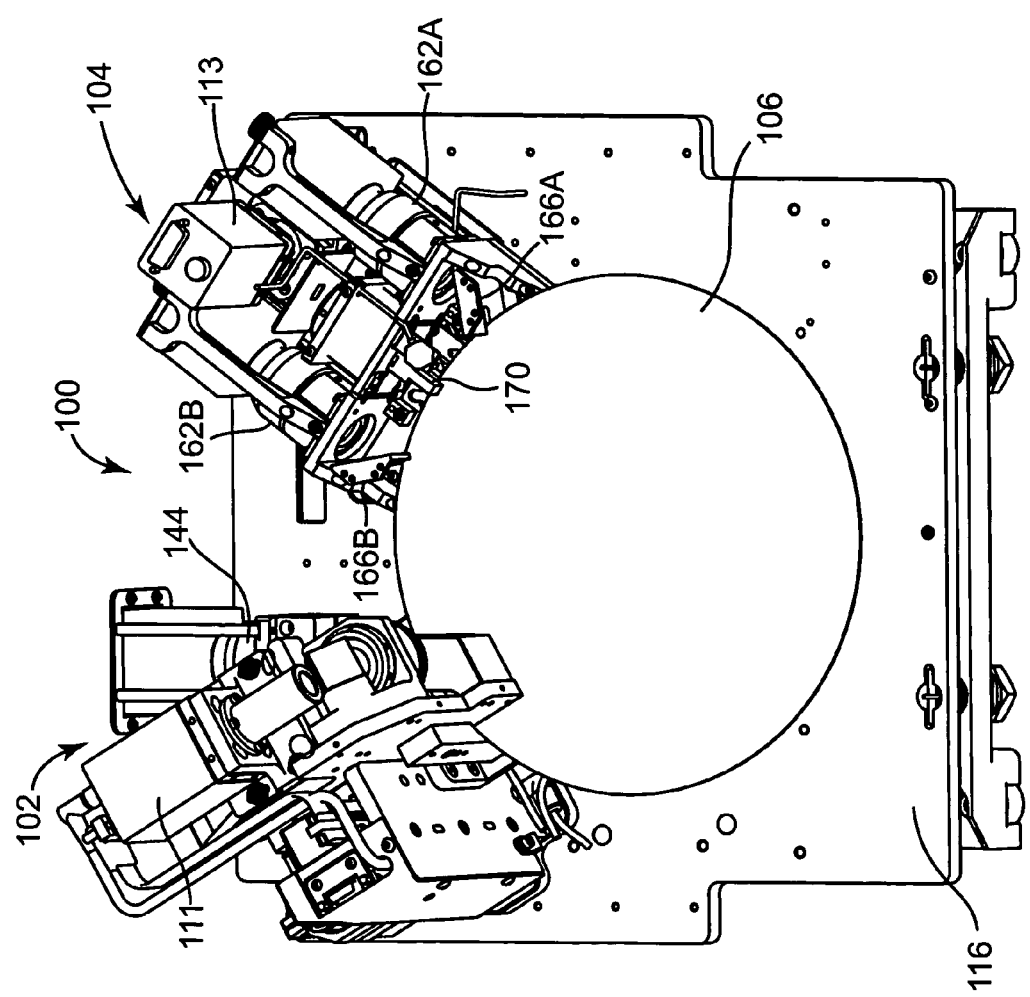
FIG. 5 is a front perspective view illustrating one embodiment of the edge inspection system.
Figure 6:
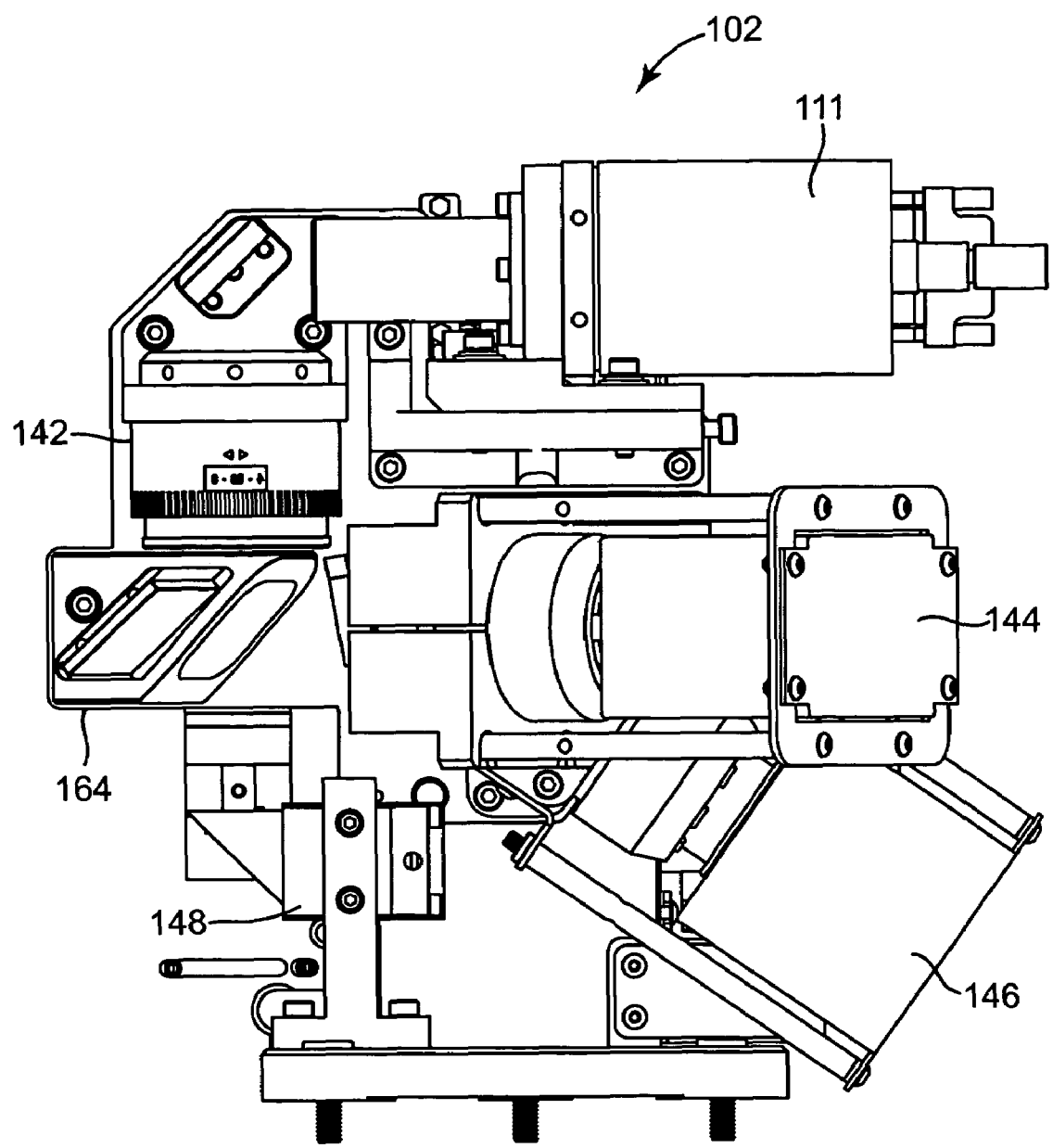
FIG. 6 is a side view illustrating one embodiment of an edge top sensor.

FIGS. 3-5 illustrate varying views of one embodiment of edge inspection system 100. FIG. 3 illustrates a top view, FIG. 4 illustrates an angled perspective view, and FIG. 5 illustrates a front perspective view of edge inspection system 100. FIG. 6 illustrates a side view of one embodiment of edge top sensor 102, and FIG. 7 illustrates a perspective view of one embodiment of edge normal sensor 104.

Edge top sensor 102 is an inspection sensor and, as illustrated in FIG. 6, includes edge top camera 111, a beamsplitter 164, optics 142, a brightfield light or strobe 144, a darkfield light or strobe 146, a backlight 148, and a servo motor and focus stage (not shown). Edge top camera 111, in one embodiment, is a color camera with the following specifications, although other parameters may be used: 10×5 mm field of view (FOV), 51 µm resolution, and 360° continuous coverage of the wafer edge in both brightfield and darkfield modes.

Figure 7:
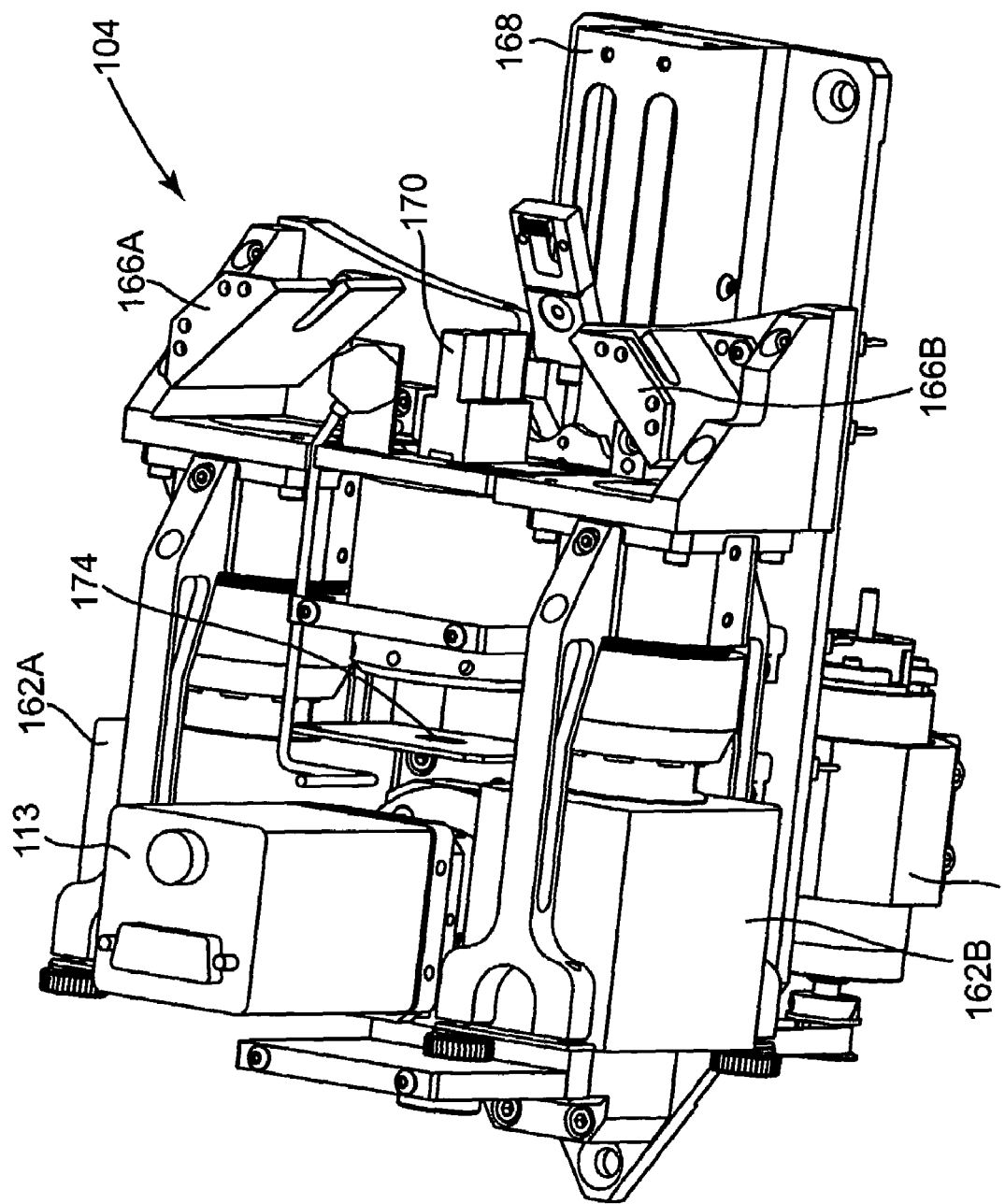
FIG. 7 is a perspective view illustrating one embodiment of an edge normal sensor.

Edge normal sensor 104 is an inspection sensor and, as illustrated in FIG. 7, includes edge normal camera 113, one or more strobes, such as strobes 162A and 162B, and mirrors 166A and 166B. Edge normal camera 113, in one embodiment, is positioned so as to look at the thin profile of wafer 106. Camera 113, in one embodiment, is a single chip color camera with the following specifications, although other parameters may be used: 4×2 mm FOV, 4 µm resolution, and 360° continuous coverage of the wafer edge in mixed mode lighting. In one embodiment, the one or more strobes 162A and 162B are incident on wafer edge bevel 129 while simultaneously incident on diffuser 170 to provide mixed mode lighting.

Edge inspection system 100 of the present invention is used in one embodiment to inspect the edge of a substrate such as a semiconductor wafer. For example, edge inspection system 100 can inspect edge 107 of wafer 106. Edge inspection system 100 is a unique system that uses multiple cameras, such as cameras 111 and 113, with corresponding strobe lights, such as strobe lights 162A and 162B for edge normal camera 113, and brightfield light 144 and darkfield light 146 (FIG. 6) for edge top camera 111. Edge top camera 111 and edge normal camera 113 are used to acquire image data around the circumference of a substrate or wafer 106 for both the top of edge 107 of wafer 106 and wafer edge bevel 129, respectively. In one embodiment, edge normal camera 113 and edge top camera 111 have 4 µm and 5 µm image resolution, respectively, and special lighting diffusers to enable the detection of defects. One such diffuser 170 is illustrated attached to edge normal camera 113 in FIG. 3.

In one embodiment, edge inspection system 100 collects or captures image data for 100% of the circumference of wafer 106 for processing and analysis. In addition, according to one form of the invention, the images are in color for better defect classification. Further, strobe lights 162A and 162B enable greater depth-of-field for edge normal camera 113, enabling easier review of wafer edge bevel 129 by not having to focus on wafer edge bevel 129. Even more, edge top camera 111 captures two passes of data around the circumference of wafer 106. The first pass is brightfield data, while the second pass is darkfield data. This enables more reliable detection of EBR line 126 for resist removal metrology and the ability to better detect and classify particles and other contaminants as either surface particles or embedded particles. In one embodiment, all of the data from a single wafer is collected in less than approximately 10 seconds and processed in less than approximately 30 seconds.

In operation of edge top sensor 102, wafer 106 is spun by motor 112. In one embodiment, wafer 106 is spun two revolutions or most preferably slightly more than two full revolutions such as 2.1 revolutions or the like to provide a bit of overlap to assure that all data is collected. In the first revolution, the brightfield strobe 144 and backlight 148 are illuminated and images are gathered around the circumference of wafer 106. The images are passed to controller 118 where algorithms process the images to look for defects, wafer center, wafer edges, EBR lines, and the notch. Edge data of wafer 106 is fed to the motion control system (not shown) of edge normal camera 113 in order to keep edge normal camera 113 in focus while edge normal camera 113 is inspecting edge 107 of wafer 106. In the second revolution, darkfield images are collected at the same positions on wafer 106 as the corresponding brightfield images.

The wafer edge data obtained by edge top camera 111 during the first revolution is used to focus edge normal camera 113 by controlling servo motor 172 to move sensor 104 on focus stage 168. In one embodiment, dual strobes 162A and 162B with diffuser 170 and a small aperture 174 enable 0.5 mm depth-of-field for edge normal camera 113. During the second revolution, the edge normal images are collected from 100% of the circumference of wafer 106. The images are passed to controller 118 where the algorithms process the images to look for defects. Furthermore, in one embodiment, edge normal camera 113 is a color camera, thus enabling better defect capture ability such as thin film variation, particles, delamination, residual resist, slurry ring, etc.

Edge inspection system 100 includes staging 110 that has support plate 108 thereon on which wafer 106 is loaded during operation. In one embodiment, staging 110 is a Continuous Rotate Stage including motor 112 and encoder 114. In one embodiment, encoder 114 is a 1.3 Million Counts/Rev encoder. In one form of the invention, stage 110 includes a vacuum to hold wafer 106 in place on support plate 108.

In one embodiment, edge inspection system 100 is packaged in an integrated metrology module of the type contemplated under draft Semiconductor Equipment and Materials (SEMI) standard 3377C for integrated metrology modules (IMM). In this embodiment, edge inspection system 100 attaches to a loadport using an interface such as a 300 mm BOLTS interface. In one embodiment, edge inspection system 100 is part of multiple inspection modules clustered about a single robot and controller, thereby reducing handling costs and inspection data flow costs. This novel multiple inspection module approach further allows more than one module of the same type to be attached to the cluster to improve throughput or add reliability.

Overall, edge inspection system 100 detects defects and variations along the edge 107 of wafer 106, such as particles, chips, cracks, delamination, copper-overflow, resist particles, embedded particles, etc. Detecting these types of defects enables either re-work, discontinuing processing, or process enhancement to achieve better yields. In one embodiment, edge inspection system 100 is very fast (in one embodiment over 100 wafers per hour), of a small form factor, low cost, robust, and offline review capable (preferably in color images).

In more detail, edge inspection system 100 performs various processes, including either or both EBR and edge of wafer (EEW) metrology measurement, chip and/or crack inspection, contamination and/or particles inspection, and delamination inspection using image processing techniques. The EBR and/or EEW metrology step involves analyzing the images to obtain the measurement from wafer edge normal 128 of wafer 106 to start 126 of resist layer 124. The chip and/or crack inspection involves analyzing the images for chips and cracks evident along wafer edge normal 128, top bevel 130, and bottom bevel 132. The contamination and/or particles inspection involves analyzing the images for anomalies found on wafer edge bevel 129 or in edge exclusion region 120 of wafer 106. The delamination inspection involves analyzing the images for layer separation evident along wafer edge normal 128, top bevel 130, or bottom bevel 132.

As to performance, many external factors such as wafer type and conditions influence performance levels such as speed and accuracy. In one embodiment, however, edge inspection system 100 has the following EBR and/or EEW metrology performance characteristics: up to and including full 360° continuous measurements (selectable amounts less than this), 1° increments, 50 µm accuracy, and 10 µm repeatability. As to chips and cracks, 100 µm or greater accuracy is provided. As to contamination and particles, 5 µm resolution and full coverage edge top and edge normal is provided. As to overall performance, according to one form of the invention, edge inspection system 100 is capable of full color defect images, multiple revolutions per inspection, approximately 20 seconds per complete inspection using both edge top 102 and edge normal 104 sensors, approximately 12 seconds for wafer handling, and approximately 120 or more wafers per hour (WPH).

Figure 8:
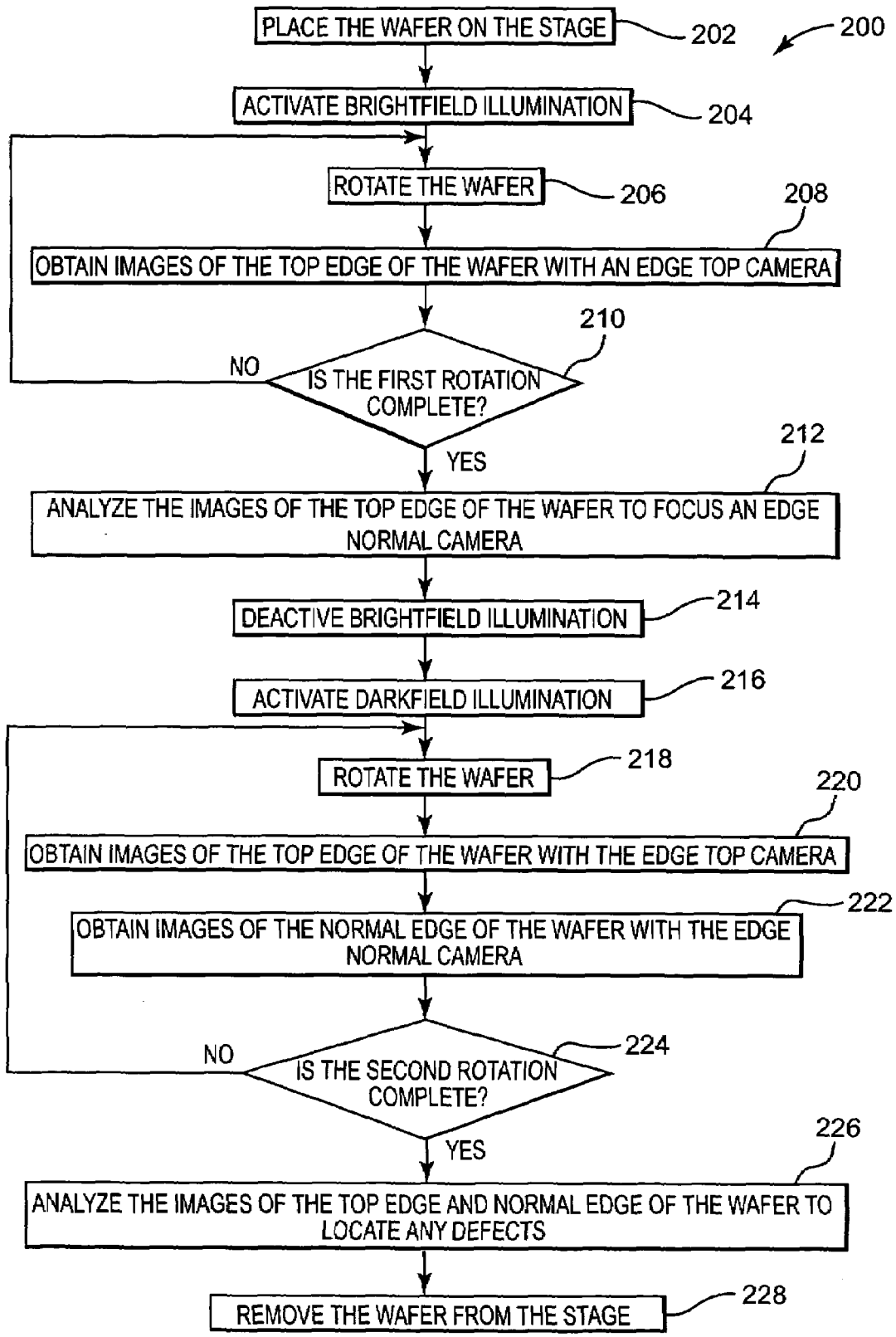
FIG. 8 is a flow diagram illustrating one embodiment of a method for inspecting the edges of semiconductor wafers.

FIG. 8 is a flow diagram illustrating one embodiment of a method 200 for detecting defects on edge 107 (FIG. 2) of semiconductor wafer 106. At 202, wafer 106 is loaded on stage 110 and held in place by support plate 108 and a vacuum. At 204, controller 118 activates brightfield illumination for sensor 102. At 206, controller 118 begins rotating wafer 106 on stage 110 using motor 112. At 208, top edge sensor 102 obtains images of the top of edge 107 of wafer 106. At 210, controller 118 determines if the first rotation of wafer 106 is completed. If the first rotation of wafer 106 is not completed, control returns to block 206 where wafer 106 continues to rotate and images continue to be obtained with edge top camera 102. If the first rotation of wafer 106 is completed, then at 212, the images of the top of edge 107 of wafer 106 are analyzed by controller 118 and used to control the position of edge normal sensor 104 to keep edge normal camera 113 in focus.

At 214, controller 118 deactivates the brightfield illumination for sensor 102. At 216, controller 118 activates the darkfield illumination for sensor 102. At 218, controller 228 rotates wafer 106. At 220, top edge camera 111 obtains images of the top of edge 107 of wafer 106. At 222, at the same time the top edge images are being obtained, normal edge camera 113 also obtains images of wafer edge bevel 129. At 224, controller 118 determines if the second rotation of wafer 106 is completed. If the second rotation of wafer 106 is not completed, control returns to block 218 where wafer 106 continues to rotate and images continue to be obtained with normal edge camera 104. If the second rotation of wafer 106 is completed, then at 226, the images of the top of edge 107 and wafer edge bevel 129 of wafer 106 are analyzed to locate any edge defects. At 228, wafer 106 is unloaded from stage 110, completing the inspection process.

Figure 9:
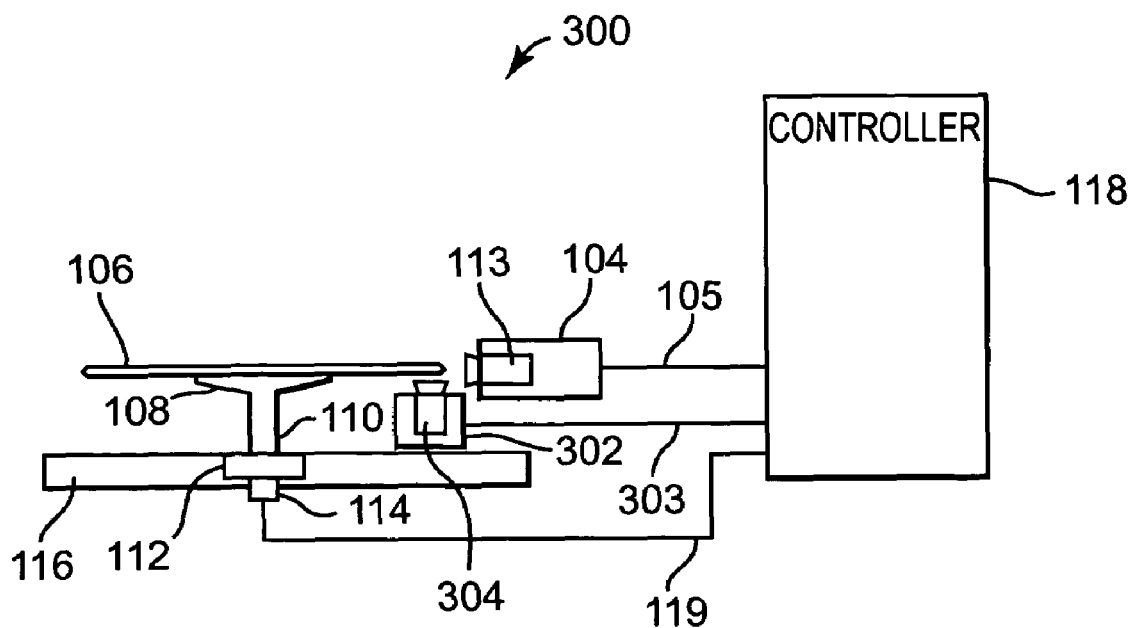
FIG. 9 is a schematic diagram illustrating an alternative embodiment of an edge inspection system.

FIG. 9 is a schematic diagram illustrating an alternative embodiment of an edge inspection system 300. Edge inspection system 300, in addition to edge normal sensor 104, controller 118, stage 110, and base 116, includes edge bottom sensor 302 in place of edge top sensor 102. Edge bottom sensor 302 includes a bottom edge camera 304. Controller 118 is electrically coupled to edge bottom sensor 302 through communication link 303.

Edge bottom sensor 302 is identical or substantially similar to edge top sensor 102, except for the location. In this embodiment, edge bottom sensor 302 is located below wafer 106 rather than above wafer 106. Edge inspection system 300 performs edge inspection in substantially the same manner as edge inspection system 100 (FIG. 1), except that edge inspection system 300 inspects the bottom of edge 107 (FIG. 2) of wafer 106 rather than the top of edge 107 of wafer 106.

Figure 10:
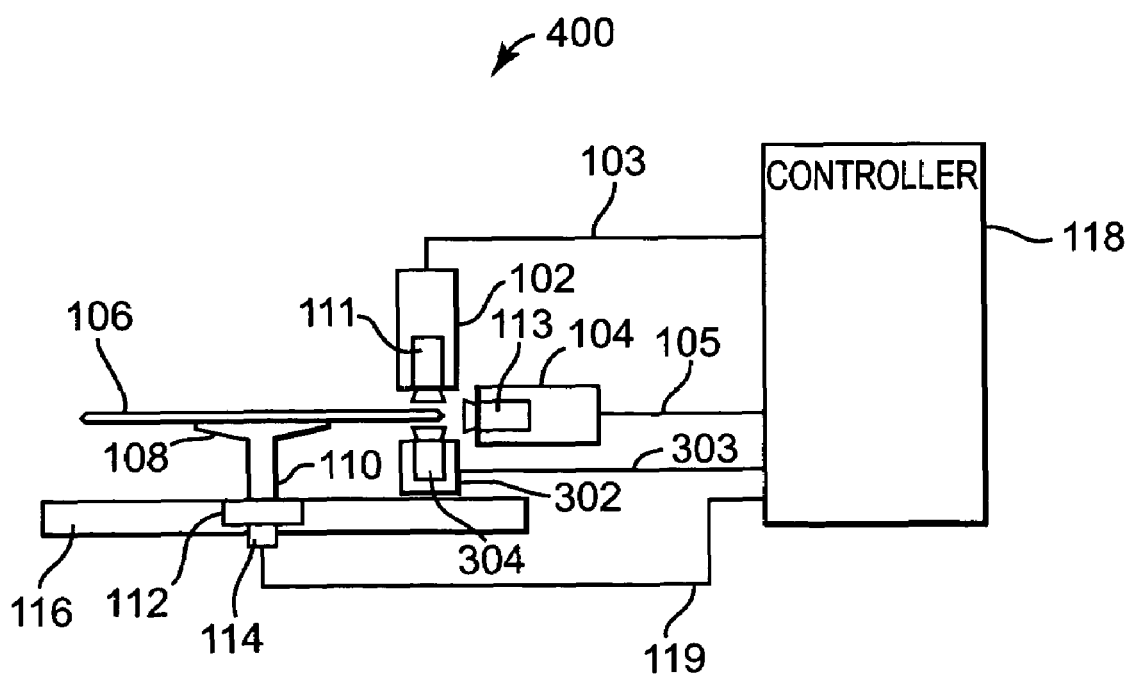
FIG. 10 is a schematic diagram illustrating another alternative embodiment of an edge inspection system.

FIG. 10 is a schematic diagram illustrating another alternative embodiment of an edge inspection system 400. Edge inspection system 400, in addition to edge top sensor 102, edge normal sensor 104, controller 118, staging 110, and base 116, includes edge bottom sensor 302.

In this embodiment, both the top and bottom edge of wafer 106 are inspected. Edge inspection system 400 performs edge inspection in substantially the same manner as edge inspection system 100 (FIG. 1), except that edge inspection system 400 inspects both the top of edge 107 (FIG. 2) and the bottom of edge 107 of wafer 106.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. A semiconductor inspection tool comprising:
   an edge top camera for obtaining images of a top surface of a wafer proximal to an outer edge of the wafer;
   an edge normal camera for obtaining images of a top bevel, normal edge, and a bottom bevel of the wafer; and
   a controller for receiving the images from the edge top camera and from the edge normal camera and for analyzing the images from the edge top camera and from the edge normal camera for wafer defects.

2. The semiconductor inspection tool of claim 1, further comprising:
   a stage for supporting the wafer, the stage adapted to rotate the wafer with respect to the edge top camera and the edge normal camera.

3. The semiconductor inspection tool of claim 2, wherein the edge top camera is adapted to obtain images providing continuous coverage of the top surface of the wafer proximal to the outer edge of the wafer per rotation of the wafer.

4. The semiconductor inspection tool of claim 2, wherein the edge normal camera is adapted to obtain images providing continuous coverage of the top bevel, normal edge, and bottom bevel of the wafer per rotation of the wafer.

5. The semiconductor inspection tool of claim 1, further comprising:
a brightfield light adapted for brightfield illumination of the top surface of the wafer.

6. The semiconductor inspection tool of claim 5, wherein the brightfield light comprises a strobe light.

7. The semiconductor inspection tool of claim 1, further comprising:
a darkfield light adapted for darkfield illumination of the top surface of the wafer.

8. The semiconductor inspection tool of claim 7, wherein the darkfield light comprises a strobe light.

9. The semiconductor inspection tool of claim 1, further comprising:
a backlight adapted for backlight illumination of the top surface of the wafer.

10. The semiconductor inspection tool of claim 1, further comprising:
a strobe light adapted for illumination of the top bevel, the normal edge, and the bottom bevel of the wafer.

11. The semiconductor inspection tool of claim 1, wherein the edge top camera comprises a color camera.

12. The semiconductor inspection tool of claim 1, wherein the edge normal camera comprises a color camera.

13. The semiconductor inspection tool of claim 1, wherein the controller is adapted to use data from images from the edge top camera to focus the edge normal camera.

14. The semiconductor inspection tool of claim 1, wherein the wafer edge defects comprise one of film variation defects, particle defects, delamination defects, residual resist defects, slurry ring defects, chip defects, and copper-overflow defects.

15. The semiconductor inspection tool of claim 1, wherein the controller is adapted to analyze the images of the top surface of the wafer to perform edge bead removal and edge exclusion metrology.

16. The semiconductor inspection tool of claim 1, wherein the controller is adapted to analyze the images from the edge normal camera to perform one of top bevel metrology and bottom bevel metrology.

17. The semiconductor inspection tool of claim 1, further comprising:
an edge bottom camera for obtaining images of a bottom surface of the water proximal to the outer edge of the wafer, wherein the controller is adapted for receiving the images from the edge top camera, the edge normal camera, and the edge bottom camera and for analyzing the images from the edge top camera, the edge normal camera, and the edge bottom camera for wafer defects.

18. A semiconductor inspection tool comprising:
an edge bottom camera for obtaining images of a bottom surface of a wafer proximal to an outer edge of the wafer;
an edge normal camera for obtaining images of a top bevels, normal edge, and a bottom bevel of the wafer; and
a controller for receiving the images from the edge bottom camera and from the edge normal camera and for analyzing the images from the edge bottom camera and from the top edge normal camera for wafer edge-defects.

19. The semiconductor inspection tool of claim 18, wherein the edge bottom camera comprises a color camera.

20. The semiconductor inspection tool of claim 18, wherein the edge normal camera comprises a color camera.

21. The semiconductor inspection tool of claim 18, wherein the controller is adapted to use data from images from the edge bottom camera to focus the edge normal camera.

22. A semiconductor inspection tool comprising:
a stage for supporting and rotating a wafer;
an edge top sensor for obtaining images of a top surface of a wafer proximal to an outer edge of the wafer;
an edge normal sensor for obtaining images of a top bevel, a normal edge, and a bottom bevel of the wafer; and
a controller for receiving the images from the edge top sensor and from the edge normal sensor and for analyzing the images from the edge top sensor and from the edge normal sensor for wafer defects.

23. The semiconductor inspection tool of claim 22, wherein the semiconductor inspection tool is adapted to inspect over 100 wafers per hour.

24. The semiconductor inspection tool of claim 22, wherein the controller is adapted to analyze the images from the edge top sensor and from the edge normal sensor for chip defects and crack defects with a 100 µm or greater accuracy.

25. The semiconductor inspection tool of claim 22, wherein the edge top sensor has a 5 µm resolution.

26. The semiconductor inspection tool of claim 22, wherein the edge normal sensor has a 4 µm resolution.

27. The semiconductor inspection tool of claim 22, wherein the stage comprises a vacuum for holding the wafer.

28. The semiconductor inspection tool of claim 22, wherein the stage comprises a motor and an encoder having up to 1.3 million counts per revolution.

29. The semiconductor inspection tool of claim 22, wherein the semiconductor inspection tool is compliant with draft Semiconductor Equipment and Materials International (SEMI) standard 3377C for integrated metrology modules (IMM).

30. A method for inspecting an edge of a semiconductor wafer, the method comprising:
rotating a wafer;
obtaining images of a top surface of a wafer proximal to an outer edge of the wafer with an edge top camera at a plurality of locations around the circumference of the wafer as the wafer rotates;
obtaining images of a top bevel, a normal edge, and a bottom bevel of the wafer with an edge normal camera at the plurality of locations around the circumference of the wafer as the wafer rotates; and
analyzing the images from the edge top camera and the edge normal camera for wafer defects.

31. The method of claim 30, wherein rotating the wafer comprises rotating the wafer a first revolution, and wherein obtaining images from the edge top camera comprises obtaining images of the top surface of the wafer proximal to the outer edge of the wafer using brightfield illumination.

32. The method of claim 31, wherein rotating the wafer comprises rotating the wafer a second revolution, and wherein obtaining images from the edge top camera comprises obtaining images of the top surface of the wafer proximal to the outer edge of the wafer using darkfield illumination.

33. The method of claim 30, further comprising:
focusing the edge normal camera using data obtained from the images of the top surface of the wafer proximal to the edge of the wafer.

34. A method for inspecting an edge of a semiconductor wafer, the method comprising:
- placing a wafer in a semiconductor wafer inspection system;
- activating brightfield illumination on atop edge of the wafer;
- obtaining images of the top edge of the wafer for a first rotation of the wafer;
- analyzing the images of the top edge of the wafer for the first rotation and using the results of the analysis to focus an edge normal camera;
- deactivating the brightfield illumination;
- activating darkfield illumination on the top edge of the wafer;
- obtaining images of the top edge of the wafer for a second rotation of the wafer;
- obtaining images of the normal edge of the wafer for the second rotation of the wafer; and
- analyzing the images of the top edge of the wafer for the first rotation, the images of the top edge of the wafer for the second rotation, and the images of the normal edge of the wafer for the second rotation for wafer edge defects.

35. The method of claim 34, wherein analyzing the images of the top edge of the wafer for the first rotation and using the results of the analysis to focus an edge normal camera comprises analyzing the images of the top edge of the wafer for the first rotation for a wafer edge and a wafer notch.

36. The method of claim 34, wherein obtaining the images of the top edge of the wafer for the first rotation, the images of the top edge of the wafer for the second rotation, and the images of the normal edge of the wafer for the second rotation comprises obtaining first color images, second color images, and third color images, respectively.

* * * * *

UNITED STATES PATENT AND TRADEMARK OFFICE
CERTIFICATE OF CORRECTION

PATENT NO. : 7,340,087 B2
APPLICATION NO. : 10/890762
DATED : March 4, 2008
INVENTOR(S) : Cory Watkins et al.

It is certified that error appears in the above-identified patent and that said Letters Patent is hereby corrected as shown below:

Column 3, line 17, delete "51 μm" and insert in place thereof -- 5 μm --.

Column 6, line 53, after "bevel," insert -- a --.

Column 7, line 48, delete "water" and insert in place thereof -- wafer --.

Column 7, line 59, delete "bevels," and insert in place thereof -- bevel, a --.

Column 7, line 64, after "wafer" delete "edge" therefor.

Column 9, line 5, delete "atop" and insert in place thereof -- a top --.

Signed and Sealed this

Tenth Day of June, 2008

JON W. DUDAS
*Director of the United States Patent and Trademark Office*